United States Patent [19]

Greene

[11] 4,415,751

[45] Nov. 15, 1983

[54] PROCESS FOR PREPARING PHENYLALKANOIC ACIDS

[75] Inventor: James M. Greene, Indianapolis, Ind.

[73] Assignee: Eli Lilly and Company, Indianapolis, Ind.

[21] Appl. No.: 361,293

[22] Filed: Mar. 24, 1982

Related U.S. Application Data

[63] Continuation-in-part of Ser. No. 248,379, Mar. 27, 1981, abandoned.

[51] Int. Cl.$^3$ ............................................. C07C 65/01
[52] U.S. Cl. ................................ 562/478; 260/465 R; 260/465 F
[58] Field of Search ......................................... 562/478

[56] References Cited

U.S. PATENT DOCUMENTS

Re. 29,608  4/1978  Evans et al. .................... 260/307 D
3,984,460  10/1976  Spivack ............................. 562/478

OTHER PUBLICATIONS

Rylander, "Catalytic Hydrogenation Over Platinum Metals", Academic Press, New York, 1967, pp. 246-249, 274-284, and 292-302.

*Primary Examiner*—Paul J. Killos
*Attorney, Agent, or Firm*—Joseph A. Jones; Arthur R. Whale

[57] ABSTRACT

Hydroxyphenylacetic acids are formed from the corresponding benzaldehydes or alkyl phenyl ketones by reduction, cyanation and hydrolysis without isolation or purification of intermediate products.

37 Claims, No Drawings

PROCESS FOR PREPARING PHENYLALKANOIC ACIDS

CROSS-REFERENCE

This application is a continuation-in-part of copending application Ser. No. 248,379, filed Mar. 27, 1981, now abandoned.

BACKGROUND OF THE INVENTION

1. Field of the Invention

This invention belongs to the field of synthetic organic chemistry, and provides a particularly advantageous process for preparing certain phenylalkanoic acids from the corresponding benzaldehydes or phenyl ketones. The process provides the desired acids in high yield and acceptable purity without isolation of intermediate products.

2. State of the Art

The individual steps of the process of this invention are similar to process steps which have been carried out in the past. For example, U.S. Pat. No. 3,882,146, of Wiegand, shows the conversion of a dimethylaminomethyl compound to an acetonitrile. Rylander, Catalytic Hydrogenation over Platinum Metals, Academic Press, New York, 1967, discusses reductions of aldehydes and ketones at length, especially at pp. 246-49, 274-84, and 292-302. An article by Short et al., Tetrahedron 29, 1931-39 (1973) shows the reductive amination of a substituted benzaldehyde to the corresponding alkylaminomethyl compound, and the subsequent conversion of that compound to the corresponding acetonitrile.

SUMMARY OF THE INVENTION

This invention provides a process for preparing an acid of the formula

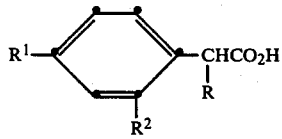

wherein R is hydrogen or $C_1$-$C_3$ alkyl; one of $R^1$ and $R^2$ is hydrogen and the other is hydroxy; provided that R is hydrogen or methyl when $R^2$ is hydroxy; comprising catalytically hydrogenating a compound of the formula

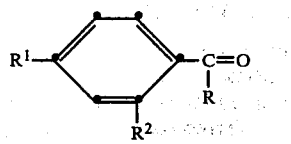

in the presence of an inert organic solvent, and optionally in the presence of an amine of the formula $HNR^3R^4$ wherein $R^3$ is $C_1$-$C_3$ alkyl and $R^4$ is hydrogen or $C_1$-$C_3$ alkyl, to prepare a compound of the formula

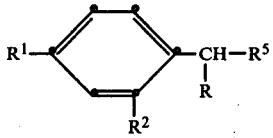

wherein $R^5$ is $-NR^3R^4$ if an amine is present, and is $-OH$ if an amine is not present; adding an alkali metal cyanide to the mixture; holding the mixture at from about 100° to about 150° until a compound of the formula

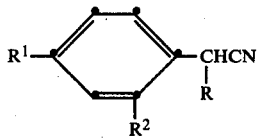

is formed; removing the solvent; adding aqueous alkali metal hydroxide; holding the mixture at about 75°-125° until the product is formed; making the mixture acid; cooling the mixture; extracting the mixture with an inert organic solvent; and isolating the acid from the organic solvent.

DESCRIPTION OF THE PREFERRED EMBODIMENT

In this document, all temperatures are described in degrees Celsius. All expressions of concentrations, ratios, proportions and the like refer to measurements by weight unless otherwise stated.

In the above statement of the invention, the term $C_1$-$C_3$ alkyl refers to the groups methyl, ethyl, propyl and isopropyl.

It is believed that the compounds which are prepared by the process of this invention are entirely familiar to organic chemists. However, the following typical products will be mentioned, to assure that the invention is fully understood.

4-hydroxyphenylacetic acid
4-hydroxy-α-isopropylphenylacetic acid
4-hydroxy-α-ethylphenylacetic acid
2-hydroxy-α-methylphenylacetic acid
4-hydroxy-α-methylphenylacetic acid
4-hydroxy-α-propylphenylacetic acid
2-hydroxyphenylacetic acid A preferred group of products of this invention includes the compounds wherein $R^1$ is hydroxy. Another preferred group of compounds includes those wherein R is hydrogen, another preferred group includes those wherein R is methyl, and a particularly preferred compound is 4-hydroxy-α-methylphenylacetic acid.

All of the starting compounds and reagents used in the process of this invention are well known to organic chemists, and can be easily purchased or prepared by methods well known in the art.

In general, only the stoichiometric amounts of the various compounds used in the process of this invention are necessary. The only important exception, as will be explained further below, is that an excess amount of base is desirable in the hydrolysis step. In the other steps, however, the exact stoichiometric amounts may be successfully used. As is usual in organic processes, it is usually advisable to use a small excess of inexpensive reagents and starting compounds, to assure that the more expensive substances are fully consumed. For this purpose, small excesses in the range of about, for example, 1.02 to 1.25 of the stoichiometric amounts may often be economically utilized.

The process of this invention will now be explained in detail. The reader should note that the individual steps are free of isolation or purification processes, except of course for the isolation of the acid which is the product of the process. It will be observed that the process is very appropriate for use in large-scale enclosed equipment, and that none of the intermediates, reagents or solvents present any unusual hazards of flammability or toxicity. The equipment needed to carry out the process is of the types commonly found in organic chemical processing plants, and no unusual corrosion problems are presented.

The concentration of the reaction mixtures is not critical. In the various steps below, an indication of the desired concentration range is given, but it is not implied that the concentrations suggested are limitations in any way on the operability of the process.

No exact times are given for the individual steps. As is always the case in chemistry, the speeds of the reactions depend very closely on the operating temperatures, and in part on other considerations such as the exact compound which is to be prepared. Indications of the times needed by the various steps are given below for the guidance of the reader, who will understand that the times stated are only indications of preferred conditions and that the times will vary markedly under slightly different operating conditions. An organic chemist will understand that the course of the reactions can be easily followed, as by thin layer chromatography, to tell when the reaction is as complete as he may desire. In some instances, the operator will wish to maximize the yields of the process by giving maximum periods of reaction time in each step; in other instances, he will wish to maximize throughput by cutting off each step at the point where it has reached an economical degree of completion.

Reduction Step

In this step, the starting compound, which is a hydroxybenzaldehyde when the group R is hydrogen, or is a phenyl alkyl ketone when R is an alkyl group, is hydrogenated catalytically in the presence of a suitable alkylamine to form the corresponding amino compound, or without an amine to form the alcohol. The amine, if used, may be either a monoalkylamine or a dialkylamine. If an amine is to be used, a dialkylamine is preferred when the starting compound is a hydroxybenzaldehyde, and a monoalkylamine is preferred when the starting compound is a ketone.

Suitable monoalkylamines include, for example, methylamine, ethylamine and propylamine; dialkylamines include ethylmethylamine, dimethylamine, diethylamine, dipropylamine and ethylpropylamine. The preferred monoalkylamine is methylamine, and the preferred dialkylamine is dimethylamine.

A preferred solvent for the reduction step is dimethylformamide. It is preferred because of its high boiling point and stability, which properties make it particularly advantageous both in the reduction step and in the following cyanation step. Other solvents, however, may be used in particular circumstances, particularly dimethylacetamide, hexamethylphosphoramide and dimethylsulfoxide. Lower alkanols are also preferred solvents for the reduction process. Methanol is particularly preferred, but ethanol, propanol and the like may also be used as desired.

Alkanols are not preferred for the cyanation step which follows, however, because of the high temperature needed in that step. Accordingly, when an alkanol is used in the reduction step, it is desirable to distill off most of the alkanol and replace it with one of the other preferred solvents before the cyanation step is begun. It will be understood that a solvent exchange of this type is readily done in the reaction vessel by merely putting it under vacuum, and that it does not affect the nonvolatile residues in the reaction mixture.

The usual hydrogenation catalysts are used in the reduction. The preferred catalyst is carbon-supported palladium, but other catalysts, such as platinum and platinum oxide may be used as desired. Hydrogen pressures from about 2 atmospheres to about 150 atmospheres are used, as is usual in the art, and the preferred process temperature is the ambient temperature. Temperatures as high even as about 100° may be used, however. A convenient concentration for the step is in the range of 1–2 gram-moles per liter, but higher and lower concentrations are readily used as may be dictated by operating convenience in a given situation.

When the reduction is complete, or is as complete as is desired, the reaction mixture is removed from the hydrogenator. The catalyst may be separated from it, usually by filtering or centrifuging the mixture, or may be left in the mixture to be filtered out later. A solvent exchange, if needed, is usually done after filtration.

Cyanation Step

An alkali metal cyanide is added to the reaction mixture from the first step. The preferred cyanide is sodium cyanide, but potassium or lithium cyanide may be used as well if desired. The mixture is then heated to an elevated temperature in the range of from about 100° to about 150°, and is stirred at that temperature until the desired acetonitrile is formed.

The preferred temperature is in the range of from about 120° to about 150°, and the optimum reaction time, when a temperature in that range is used, is about 4 to 8 hours.

When the cyanation step has gone to the desired degree of completion, the solvent is distilled from the reaction mixture, as by putting the mixture under vacuum while the vessel is heated. It is not necessary to continue the distillation until the mixture is analytically free of solvent; the later hydrolysis step will hydrolyze and remove the remaining solvent, especially when the solvent is dimethylformamide, so that residual solvent does not interfere with the isolation of the final product.

The product from the cyanation step, after the solvent has been distilled, is a thick oily or greasy residue.

HYDROLYSIS STEP

In this step, the phenylacetonitrile compound is converted to the desired carboxylic acid by a basic hydrolysis in the presence of an aqueous solution of an alkali metal hydroxide. The preferred base is sodium hydroxide, but potassium and lithium hydroxides may be used as well. The reaction mixture is most easily prepared by simply adding the aqueous base to the residue remaining after the distillation of solvent from the cyanation step reaction mixture.

It is advisable to use excess base in the hydrolysis. At least about 1.5 moles of base should be used for each mole of starting compound. Larger amounts of base may be required if the residue contains residual solvent, especially dimethylformamide, which must be hydrolyzed. A large excess of base is not harmful, and so any amount of base may be used if desired, even up to 10X or more.

The concentration of the aqueous solution of base is not critical. Relatively high concentrations, from about 10% to about 40%, are satisfactory and are preferred because of the economy and convenience of such operation. Lower concentrations can be used but are not preferred.

The basic mixture is heated to a temperature from about 75° to about 125° to accomplish the hydrolysis. Operation under pressure is of course necessary if a temperature above the boiling point is to be used. It is preferred to operate at the reflux temperature of the mixture, about 100°. Reaction times in the range of about 4 to 8 hours have been found to give essentially complete hydrolysis at the reflux temperature; operation at higher temperatures will, of course, allow shorter periods of time in the hydrolysis step.

When the hydrolysis has gone as close to completion as is desired, the reaction mixture is worked up. The first step in the preferred workup procedure is to make the mixture acid, preferably with an inexpensive mineral acid such as hydrochloric acid. Other strong acids may of course be used, so long as the neutralization product of the acid and the base used in the hydrolysis step is a water-soluble salt. Accordingly, sulfuric acid, trifluoroacetic acid, phosphoric acid and the like may be used as may be convenient in the circumstances. The mixture should be acidified to a pH in the range of 2.

In some instances, it is helpful to decolorize the product before it is isolated. Activated charcoal has been found to be effective for the purpose, and a particularly advantageous point to apply it is at the end of the hydrolysis step, while the product is still in the water solution. The decolorizing agent is conveniently added either before or after the reaction mixture is made acid, and is filtered out as usual.

It will be understood that the highly basic hydrolysis conditions are corrosive to glass or glass-lined equipment. Accordingly, the use of such vessels is not recommended; stainless steel is quite satisfactory. If glass is used, some amount of silicate will probably be leached into the reaction mixture and will create a difficult problem. When the mixture is made acid, it will precipitate and seriously interfere with isolating the product. The best procedure, where glass must be used, is to filter the acid mixture at high temperature, about 75°–125°, to remove the silicates from the product solution.

Another excellent expedient to deal with silicates is to add a portion of the extraction solvent to the cool acid mixture and filter the two-phase mixture resulting. The solvent will dissolve the product which crystallizes upon cooling, so that the silicate precipitate can be readily filtered out.

The aqueous solution is then cooled to a temperature which approximates ambient temperature, and is extracted with an inert organic solvent. The preferred solvents are esters, especially ethyl acetate. Other solvents can be used as well, such as ethers, including tetrahydrofuran and diethyl ether, for example. Obviously, the extracting solvent must be water-immiscible, and must have adequate solvency for the phenylacetic acid. The amount of solvent should preferably be in the range of from about 500 ml. per gram-mole of starting compound to about 2.5 liters per gram-mole of starting compound. The exact amount of solvent is not critical, but can be adjusted as may be convenient in a given instance, and in accordance with the relative value of extremely complete extraction of the product, as compared with the cost of solvent. It is advantageous, of course, to extract the mixture 2 or more times, adding the solvent in portions.

Finally, the product phenylacetic acid is isolated from the organic solvent. The isolation may be carried out by simply evaporating the solvent, leaving the product as the residue. To do so is difficult in large scale operation, however, and any of a number of expedients may be used. For example, the solvent can be evaporated, and the product can then be taken up as a suspension in a non-solvent such as hexane and recovered by filtration or centrifugation. Alternatively, the residual product can be dissolved in a relatively weak solvent for it, such as, for example, warm toluene or xylene. The addition of an antisolvent such as hexane or another alkane, accompanied by chilling the solution, will precipitate the product as a fine crystal, which is recovered by filtration or centrifugation. Still other expedients for isolating the product, such as evaporating the solvent from it on a heated drum dryer and scraping the product off the drum, will occur to those who are skillful in process chemistry.

As the examples below illustrate, the process of this invention will easily produce the phenylacetic acids in overall yields of 85–95%, and in excellent purity.

The products of this process are used as intermediates for the preparation of pharmaceuticals. U.S. Reissue Pat. No. 29,608 shows a group of benzoxazoles which are analgesics and antiinflammatories, and which have a carboxylic acid group, such as that of the 4-hydroxy acids produced by this invention, at the 5- or 6-position of their phenyl ring. The acids are converted to those benzoxazoles by the following steps:

(A) Nitrating the product of this invention with mixed nitric and sulfuric acids to prepare the corresponding 4-hydroxy-3-nitrophenylacetic acid;
(B) Reduction of the nitro group, as by catalytic hydrogenation or with a chemical agent such as iron-hydrochloric acid, to give the 3-amino-4-hydroxyphenylacetic acid;
(C) Acylation of the amino group to give the corresponding 3-carboxamido-4-hydroxyphenylacetic acid, where the amido group bears the group which will form the 2-substituent of the final benzoxazole;
(D) Cyclization of the above compound, as at an elevated temperature or in the presence of an acidic agent to give the desired benzoxazole pharmaceutical.

The above process steps for the formation of the benzoxazole are explained, in general, in the above mentioned reissue patent.

The 4-hydroxy product of the process of this invention wherein R is hydrogen is also used as an intermediate in preparing certain β-lactam antibiotics, particularly those taught in U.S. Pat. Nos. 4,138,486 and 4,201,782, both of Shionogi and Co. The compounds of those patents are oxa-β-lactam compounds, having a carboxy(4-hydroxyphenyl)acetamido side chain. The 4-hydroxyphenylacetic acid prepared by this invention is a useful starting compound to prepare the side chain group, as explained by Greene and Bunnell in U.S. Patent Application No. 203,736. It is there explained that the phenylacetic acid is esterified with a benzyl halide to give the corresponding benzyl 4-hydroxyphenylacetate, the hydroxy group of which is then protected. The α-carbon of the acetate is then carboxylated, as by carbon dioxide gas in the presence of a very strong base at a very low temperature, and the resulting carboxy(4-protected-oxyphenyl)acetate is used to acylate the nucleus of the desired antibiotic. The acylation and the necessary deprotection of the antibiotic is taught in the above-mentioned U.S. Pat. No. 4,201,782.

The product of this process wherein R is hydrogen and $R^2$ is hydroxy is an intermediate in the synthesis of nocardicin A, a monocyclic β-lactam antibiotic, as taught by Boucherot and Pilgrim, *Tet. Let.* 5063-66 (1979). The compound is also useful to promote the rooting of plant cuttings, Vazquez et al., *An. Edafol. Agrobiol.* 37(5-6), 441-44 (1978); *C.A.* 90, 17550k (1979).

The product wherein R is methyl and $R^2$ is hydroxy is an intermediate in the synthesis of certain dibenzoxepins having pharmaceutical uses. Ueno et al., German OLS No. 2,435,613, *C.A.* 82, 170741c (1975). The product is converted to an ether with 2-carboxytoluene, and the ether is cyclized with polyphosphoric acid and the resultant product is reduced.

The following examples further explain the process of this invention, to assure that the reader can carry it out successfully.

EXAMPLE 1

4-hydroxy-α-methylphenylacetic acid

A 27.2 g. portion of 4-hydroxyacetophenone was dissolved in 100 ml. of dimethylformamide, and the solution was cooled to 5°. To it were added 12.4 g. of anhydrous methylamine and 5 g. of 5% palladium/carbon hydrogenation catalyst. The mixture was put in a Parr hydrogenator under 50 psig. of hydrogen at 45°, and was shaken at constant temperature for 18 hours. The reaction mixture was then filtered, and to the filtrate was added 10.8 g. of sodium cyanide. The mixture was heated to 140°, and was held at that temperature with stirring for 5 hours. The mixture was then put under vacuum and was distilled down to a total weight of 54 g.

To the residue in a Pyrex flask was added 75 ml. of 50% aqueous sodium hydroxide and 75 ml. of water. The mixture was stirred under reflux for 8 hours. The solution was cooled to ambient temperature, and was acidified to pH 2 by the addition of concentrated hydrochloric acid. One hundred ml. of additional water was added, the mixture was heated with stirring to reflux, and 2.7 g. of activated carbon was added. The mixture was stirred at the reflux temperature for 30 minutes, and was filtered. The filtrate was cooled to near the ambient temperature, and was extracted with two 100 ml. portions of ethyl acetate. The organic layers were combined, and were evaporated under vacuum to obtain 39 g. of residue. To it was added 100 ml. of toluene, and the suspension was stirred for a time, after which 100 ml. of hexane was added. The resulting slurry was stirred in an ice bath for 1 hour and was filtered, and the solids were dried under vacuum at 45° to obtain 28.2 g. of the desired product, a yield of 85% of the theoretical yield. Its melting point was 128°-130°.

EXAMPLE 2

4-hydroxy-α-methylphenylacetic acid

The process of this example was carried out substantially according to the process of Example 1, except that, after the hydrolysis reaction mixture had been made acid with hydrochloric acid, and then heated to reflux, 3 g. of activated carbon was added and it was stirred under reflux for 30 minutes. The mixture was then filtered through a filter aid pad, using a steam-jacketed Buchner funnel, and the filtrate was cooled and extracted twice with 125 ml. portions of ethyl acetate. The ethyl acetate layers were combined and evaporated, and the product was recovered and dried as described in Example 1 to obtain 28.3 g. of the desired product, equivalent to 85% of the theoretical yield of the process. The product was identical to that of Example 1.

EXAMPLE 3

4-hydroxyphenylacetic acid

A 24.4 g. portion of 4-hydroxybenzaldehyde was dissolved in 100 ml. of dimethylformamide, and the solution was cooled in an ice bath. To it was added 18 g. of anhydrous dimethylamine, and 0.1 g. of platinum oxide hydrogenation catalyst. The mixture was put under 50 psig of hydrogen in an agitated hydrogenator for 1 hour and 15 minutes, during which time it took up 16 psi of hydrogen, the theoretical uptake. The mixture was then filtered into another container, and the hydrogenator and filter were washed with 20 ml. of additional dimethylformamide. To the filtrate was added 10.8 g. of sodium cyanide, and the mixture was stirred at 130° for 6 hours.

The solvent was then removed under vacuum at 80° to obtain 49.6 g. of a dark residue. To it were added 150 ml. of water and 20 g. of sodium hydroxide pellets in a Pyrex flask, and the aqueous mixture was stirred under reflux for 6 hours. It was then cooled to ambient temperature, and its pH was adjusted to 1.8 by the addition of about 60 ml. of concentrated hydrochloric acid. Six g. of activated carbon was added, and the mixture was heated briefly to reflux. It was then filtered at the boiling point, and the filter was washed with 50 ml. of hot water. The filtrate was then cooled, and was extracted with three 100 ml. portions of ethyl acetate. The organic layers were combined, washed with 50 ml. of water and dried over magnesium sulfate. The organic solution was then concentrated under vacuum to a weight of 70 g., and to the residue was slowly added 150 ml. of toluene, with stirring and cooling. The mixture was then stirred for one hour and filtered, and the solids were washed with cold toluene and dried under vacuum to obtain 25.6 g. of the desired product, m.p. 149°-152°. The yield was 84.4% of theoretical.

EXAMPLE 4

4-hydroxy-α-methylphenylacetic acid

A 13.6 g. portion of 4-hydroxyacetophenone was dissolved in 50 ml. of dimethylformamide, and 0.1 g. of sodium hydroxide and 2.5 g. of 5% palladium-on-carbon hydrogenation catalyst was added. The mixture was placed in a Parr hydrogenator at 45° for 3.5 hours, with shaking, and was then shaken at ambient temperature for 16.5 hours. The mixture was then filtered to remove the catalyst, and the solution was added to 5.4 g. of sodium cyanide in a Pyrex flask. The mixture was stirred at 130° for 6 hours, and was then evaporated under vacuum to obtain an oily residue. The residue was dissolved in 38 ml. of 50% aqueous sodium hydroxide and 38 ml. of water, and was stirred under reflux for 8 hours. Its pH was then adjusted to 2.0 with concentrated hydrochloric acid, 50 ml. of water was added, and the mixture was heated to reflux. It was filtered at the reflux temperature through a filter aid pad, and the filtrate was cooled and extracted twice with 125 ml. portions of ethyl acetate. The organic layers were combined and evaporated under vacuum to an oil. To it was added 50 ml. of toluene, followed by 50 ml. of hexane. The product crystallized within a few minutes, and the suspension was stirred for 1 hour before it was filtered. The solids were dried under vacuum at 40° to obtain 14.5 g. of the desired product, identical to that of Example 1. Its melting point was 127°–129°, and the yield was 85.8% of the theoretical yield.

EXAMPLE 5

4-hydroxy-α-methylphenylacetic acid

The process of Example 4 was repeated through the hydrogenation and cyanation steps, except that the dimethylformamide was removed under vacuum after the hydrogenation step to examine the product, and was replaced with the same amount of dimethylformamide after analysis.

After the cyanation step, the solvent was removed under vacuum to obtain a residue, which was dissolved in 20 ml. of 50% aqueous sodium hydroxide and 20 ml. of water. The mixture was stirred at the reflux temperature for 8 hours, and was then made acid to pH 2.0 with concentrated hydrochloric acid. To it was added 75 ml. of ethyl acetate, and the resulting two-phase mixture was filtered through a filter-aid pad. The pad was washed with 45 ml. of additional ethyl acetate, and the water layer of the filtrate was washed with 35 ml. of ethyl acetate. The organic layers were combined and washed with 50 ml. of water, and then the solvent was removed under vacuum to obtain an oil. Sixty ml. of toluene was added slowly to the oil, and it was allowed to stand until it crystallized. Sixty ml. of hexane was then added, and the mixture was left in an ice bath for 1 hour to crystallize completely. It was filtered, and the solids were washed with 30 ml. of hexane and dried under vacuum at 40° to obtain 14.0 g. of product, containing 0.36% of water and 0.32% of sodium chloride, a yield of 84.0% of theoretical. The product was substantially identical to that of Example 1.

EXAMPLE 6

4-hydroxy-α-methylphenylacetic acid

To 50 ml. of methanol were added 13.6 g. of 4-hydroxyphenylacetophenone and 2.5 g. of 5% palladium on alumina hydrogenation catalyst. The mixture was put under 4 atmospheres of hydrogen pressure and shaken at 40° for 2.5 hours, at which time the hydrogenation was found to be complete by nmr analysis. The mixture was filtered to remove the catalyst, and substantially all of the methanol was removed under vacuum. Seventy-five ml. of dimethylformamide and 5.4 g. of sodium cyanide were added, and the mixture was stirred for 1 hour at 130°. The mixture was then allowed to stand overnight, and the solvent was removed under vacuum. To the residue was added 20 ml. of 50% sodium hydroxide solution and 20 ml. of water. The aqueous mixture was then heated under reflux for 5.5 hours, and was then cooled and made acid to pH 2.0 with hydrochloric acid. To it was added 75 ml. of ethyl acetate, and the 2-phase mixture was stirred for 5 minutes. It was then filtered through a filter aid pad, and the pad was rinsed with 50 ml. of water. The organic layer of the filtrate was separated, dried over sodium sulfate and evaporated under vacuum to dryness. The residue was taken up in 50 ml. of toluene and 50 ml. of hexane, and stirred in an ice bath. Filtration gave 13.64 g. of the desired product, m.p. 129°–132°, which product was substantially identical to that of Example 1. The yield was 82.4% of the theoretical yield.

I claim:

1. A process for preparing an acid of the formula

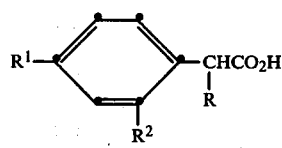

wherein R is hydrogen or $C_1$–$C_3$ alkyl; one of $R^1$ and $R^2$ is hydrogen and the other is hydroxy; provided that R is hydrogen or methyl when $R^2$ is hydroxy; comprising catalytically hydrogenating a compound of the formula

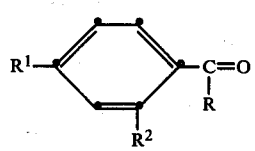

in the presence of an inert organic solvent, and optionally in the presence of an amine of the formula $HNR^3R^4$ wherein $R^3$ is $C_1$–$C_3$ alkyl and $R^4$ is hydrogen or $C_1$–$C_3$ alkyl, to prepare a compound of the formula

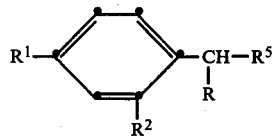

wherein $R^5$ is —$NR^3R^4$ if an amine is present, and is —OH if an amine is not present; adding an alkali metal cyanide to the mixture;
holding the mixture at from about 100° to about 150° until a compound of the formula

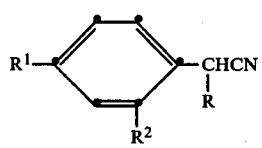

is formed; removing the solvent; adding aqueous alkali metal hydroxide; holding the mixture at about 75°–125° until the product is formed; making the mixture acid; cooling the mixture; extracting the mixture with an inert organic solvent; and isolating the acid from the organic solvent.

2. A process of claim 1 wherein an amine is used.
3. A process of claim 2 for preparing an acid wherein $R^1$ is hydroxy.
4. A process of claim 3 for preparing an acid wherein R is hydrogen.

5. A process of claim 3 for preparing an acid wherein R is methyl.

6. A process of either claim 2 or 5 wherein the amine is methylamine.

7. A process of either claim 2 or 4 wherein the amine is dimethylamine.

8. A process of claim 2 wherein the amine is methylamine.

9. A process of claim 2 wherein the amine is dimethylamine.

10. A process of any one of claims 2-5 or 8-9 wherein the inert organic solvent is dimethylformamide.

11. A process of any one of claims 2-5 or 8-9 wherein the alkali metal cyanide is sodium cyanide.

12. A process of any one of claims 2-5 or 8-9 wherein the alkali metal hydroxide is sodium hydroxide.

13. A process of any one of claims 2-5 or 8-9 wherein the mixture is held at about the reflux temperature after the addition of the aqueous alkali metal hydroxide.

14. A process of any one of claims 2-5 or 8-9 wherein the extraction is with an inert organic solvent which is an ester or an ether.

15. A process of claim 10 wherein the alkali metal cyanide is sodium cyanide.

16. A process of claim 15 wherein the alkali metal hydroxide is sodium hydroxide.

17. A process of claim 16 wherein the mixture is held at about the reflux temperature after the addition of the aqueous sodium hydroxide.

18. A process of claim 17 wherein the extraction is with an inert organic solvent which is an ester or an ether.

19. A process of claim 18 wherein the amine is dimethylamine.

20. A process of claim 18 wherein the amine is methylamine.

21. A process of claim 1 wherein no amine is used.

22. A process of claim 21 for preparing an acid wherein $R^1$ is hydroxy.

23. A process of claim 22 for preparing an acid wherein R is hydrogen.

24. A process of claim 22 for preparing an acid wherein R is methyl.

25. A process of any one of claims 21-24 wherein the inert organic solvent is dimethylformamide.

26. A process of any one of claims 21-24 wherein the alkali metal cyanide is sodium cyanide.

27. A process of any one of claims 21-24 wherein the alkali metal hydroxide is sodium hydroxide.

28. A process of any one of claims 21-24 wherein the mixture is held at about the reflux temperature after the addition of the aqueous alkali metal hydroxide.

29. A process of any one of claims 21-24 wherein the extraction is with an inert organic solvent which is an ester or an ether.

30. A process of claim 25 wherein the alkali metal cyanide is sodium cyanide.

31. A process of claim 30 wherein the alkali metal hydroxide is sodium hydroxide.

32. A process of claim 31 wherein the mixture is held at about the reflux temperature after the addition of the aqueous sodium hydroxide.

33. A process of claim 32 wherein the extraction is with an inert organic solvent which is an ester or an ether.

34. A process of claim 26 wherein the solvent in the reduction step is methanol, which solvent is removed after the reduction step and replaced with dimethylformamide.

35. A process of claim 34 wherein the alkali metal hydroxide is sodium hydroxide.

36. A process of claim 35 wherein the mixture is held at about the reflux temperature after the addition of the aqueous sodium hydroxide.

37. A process of claim 36 wherein the extraction is with an inert organic solvent which is an ester or an ether.

* * * * *